US006054560A

United States Patent [19]

Deng et al.

[11] Patent Number: 6,054,560

[45] Date of Patent: Apr. 25, 2000

[54] MITOGEN ACTIVATED PROTEIN KINASE, FRK

[75] Inventors: Tiliang Deng, Gainesville, Fla.; Michael Karin, San Diego, Calif.

[73] Assignee: The Regents of the University of California, Oakland, Calif.

[21] Appl. No.: 09/193,797

[22] Filed: Nov. 17, 1998

Related U.S. Application Data

[60] Continuation of application No. 08/707,874, Sep. 9, 1996, Pat. No. 5,837,451, which is a division of application No. 08/315,067, Sep. 29, 1994, Pat. No. 5,925,557.

[51] Int. Cl.[7] .................................................. C07K 16/40

[52] U.S. Cl. ...................................... 530/387.1; 435/194

[58] Field of Search ......................... 530/387.1; 435/194

[56] References Cited

U.S. PATENT DOCUMENTS 5,605,808 2/1997 Karin et al. .............................. 435/15

FOREIGN PATENT DOCUMENTS

WO/8908114 9/1989 WIPO .

OTHER PUBLICATIONS

Bannister et al, Nucleic Acid Res., 22, 5173–5176, 1994.

Chen et al, Proc. Natl. Acad. Sci. USA, 90, 10952–10956, 1993.

Deng et al., "C–Fos transcriptional activity stimulated by H–Ras–activated protein kinase distinct from JNK and ERK", Nature, 371:171–175, 1994.

Taylor et al., "Identification of a nerve growth factor—and epidermal growth factor–regulated protein kinase that phosphorylates the protooncogene product c–Fos", Proc. Natl. Acad. Sci., USA, 90:368–37, 1993.

Richard A. Lerner, Tapping the immunological repertoire to produce to produce antibodies of predetermined specificity Nature, 299:592–596, 1982.

*Primary Examiner*—John L. LeGuyader

*Attorney, Agent, or Firm*—Gray Cary Ware & Freidenrich LLP; Lisa A. Haile

[57] ABSTRACT

An isolated c-Fos regulating kinase polypeptide (FRK) characterized by having a molecular weight of 88 kD as determined by reducing SDS-PAGE, having threonine and serine kinase activity, phosphorylating the c-Fos activation domain and polynucleotide sequences and method of detection of FRK are provided herein. Also described are methods for identifying compositions which affect FRK activity, thereby affecting c-Fos activation and subsequent activation of genes associated with AP-1 sites.

6 Claims, 9 Drawing Sheets

MITOGEN ACTIVATED PROTEIN KINASE, FRK

This application is a continuation of U.S. application Ser. No. 08/707,874, filed Sep. 9, 1996, now issued as U.S. Pat. No. 5,837,451, which is a divisional of U.S. application Ser. No. 08/315,067, filed Sep. 29, 1994, now issued as U.S. Pat. No. 5,925,557.

This invention was made with Government support under Grant Nos. CA50528 and ES-06376 awarded by the National Institutes of Health; Grant No. MG-202393 awarded by the American Cancer Society, Council for Tobacco Research and Grant No. 3RT-0138 awarded by the Tobacco-Related Disease Research Program. The Government has certain rights in this invention.

BACKGROUND OF THE INVENTION

1. Field of the Invention

This invention relates generally to the field of protein kinases, oncogenes and oncoproteins and, specifically, to a protein kinase which phosphorylates and potentiates the activity of c-Fos.

2. Description of Related Art

A number of viral and cellular genes have been identified as potential cancer genes, collectively referred to as oncogenes. The cellular homologs of viral oncogenes, the proto-oncogenes or c-oncogenes, act in the control of cell growth and differentiation or mediate intracellular signaling systems. The products of oncogenes are classified according to their cellular location, for example, secreted, surface, cytoplasmic, and nuclear oncoproteins.

Proto-oncogenes which express proteins which are targeted to the cell nucleus make up a small fraction of oncogenes. These nuclear proto-oncoproteins typically act directly as transactivators and regulators of RNA and DNA synthesis. Nuclear oncogene products have the ability to induce alterations in gene regulation leading to abnormal cell growth and ultimately neoplasia. Examples of nuclear oncogenes include the myc, ski, myb, fos and jun genes.

The c-Fos protein, encoded by the c-fos proto-oncogene, is an important component of the dimeric, sequence specific, transcriptional activator, AP-1. Many proteins cooperate with each other in the activation of transcription from specific promoters. Through this cooperation, a gene can be transcribed and a protein product generated. Members of the Fos proto-oncogene family, along with members of the Jun gene family, form stable complexes which bind to DNA at an AP-1 site. The AP-1 site is located in the promoter region of a large number of genes. Binding of the Fos/Jun complex activates transcription of a gene associated with an AP-1 site. In cells that have lost their growth regulatory mechanisms, it is believed that this Fos/Jun complex may "sit" on the AP-1 site, causing overexpression of a particular gene. Since many proliferative disorders result from the overexpression of an otherwise normal gene, such as a proto-oncogene, it would be desirable to identify compositions which interfere with the excessive activation of these genes.

Ras proteins exert their mitogenic and oncogenic effects by activating protein kinase cascades leading to phosphorylation of nuclear transcription factors. AP-1, as described above, is a heterodimeric complex of Jun and Fos proteins, which activates mitogen-inducible genes and is also a major nuclear target of Ras. Ras can stimulate AP-1 activity through c-fos induction (Angel and Karin, *Biophys. Acta.,* 1072:129–157, 1991; Herrlich and Ponta, *Trends Genet.,* 5:112–116, 1989), a process likely to be mediated by the ERK1 and ERK2 mitogen activated protein (MAP) kinases (G. Thomas, *Cell,* 68:3–6, 1992), through phosphorylation of Elk-1/TCF (Sharrocks, and Shaw, *Nature,* 358:414–417, 1992; Wynne, et al., *Cell,* 73:381–393, 1993; Zinck, et al., *EMBO J.,* 12:2377–2387, 1993). However, besides inducing fos and jun gene transcription, mitogens and Ras proteins enhance AP-1 activity through phosphorylation of c-Jun (Binetruy, et al., *Nature,* 351:122–127, 1991; Smeal, et al, *Nature,* 354:494–496, 1991; Pulverer, et al., *Nature,* 353:683–689, 1991). Through an autoregulatory loop, phosphorylation of the c-Jun activation domain leads to c-jun induction (Angel and Karin, supra). Recently, Ras- and UV-responsive protein kinases that phosphorylate c-Jun on serines (Ser) 63 and 73 and stimulate its transcriptional activity were identified (Hibi, et al., *Genes & Dev.,* 7:2135–2148, 1993).

These proline-directed kinases, termed JNK, for c-Jun-N-terminal kinase, are novel MAP kinases (Derijard, et al., *Cell,* 75:1025–1037, 1994). It is not clear, however, whether c-Jun is the only recipient and whether JNK is the only transducer of the Ras signal to AP-1 proteins. A short sequence surrounding the major JNK phosphorylation site of c-Jun (Ser73) is conserved in c-Fos and is part of its activation domain (Sutherland, et al, *Genes & Dev.,* 6:1810–1819, 1992). The present invention demonstrates that Ras does indeed augment c-Fos transcriptional activity through phosphorylation at Thr232, the homolog of Ser73 of c-Jun. However, this is mediated by a novel Ras- and mitogen-responsive proline-directed protein kinase that is different from JNKs and ERKs.

For many years, various drugs have been tested for their ability to alter the expression of genes or the translation of their messages into protein products. One problem with existing drug therapy is that it tends to act indiscriminately and affects healthy cells as well as neoplastic cells. This is a major problem with many forms of chemotherapy where there are severe side effects primarily due to the action of toxic drugs on healthy cells.

In view of the foregoing, there is a need to identify specific targets in the abnormal cell which are associated with the overexpression of genes whose expression products are implicated in cell proliferative disorders, in order to decrease potential negative effects on healthy cells. The present invention provides such a target.

SUMMARY OF THE INVENTION

The present invention provides a novel Fos regulating protein kinase (FRK) which phosphorylates c-Fos and potentiates its activity. FRK is characterized by having a molecular weight of about 88 kD (as determined by reducing SDS-polyacrylamide gel electrophoresis (PAGE)) and having threonine and serine kinase activity. Specifically, FRK phosphorylates threonine residue 232 of c-Fos.

Since the product of the fos proto-oncogene is a transactivator protein which binds at AP-1 sites, regulation of c-Fos activation may be important in affecting normal gene expression and growth control in a cell. The discovery of FRK provides a means for identifying compositions which affect FRK activity, thereby affecting c-Fos activation and subsequent activation of genes associated with AP-1 sites.

The identification of FRK now allows the detection of the level of specific kinase activity associated with activation of c-Fos and AP-1. In addition, the invention provides a method of treating a cell proliferative disorder associated with FRK by administering to a subject with the disorder, a therapeutically effective amount of a reagent which modulates FRK activity.

The invention also provides a synthetic peptide comprising the FRK binding region on c-Fos which corresponds to amino acids 226–236 ($_{226}$GLPEASTPES-E$_{236}$(SEQ ID NO:1)). The peptide is useful as a competitive inhibitor of the naturally occurring c-Fos in situations where it is desirable to decrease the amount of c-Fos activation by FRK.

DETAILED DESCRIPTION OF THE INVENTION

Figure 1A:
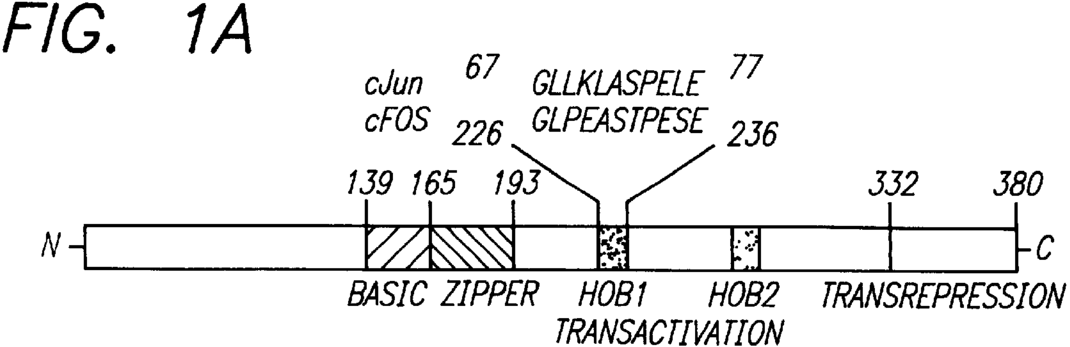
FIGS. 1A and B show diagrams illustrating the salient features of c-Fos and the GHF1-cFos (210–313) chimera, including the position of the HOB1 and HOB2 regions and a sequence alignment of the HOB1 regions of c-Jun and c-Fos.

The present invention provides a novel protein kinase (FRK) which binds to a well-defined region of the c-Fos proto-oncoprotein and phosphorylates a site within its activation domain. The phosphorylation of this site increases the ability of c-Fos to stimulate transcription and mediate oncogenic transformation.

The activity of c-Fos is regulated by phosphorylation. Various stimuli, including transforming oncogenes and mitogens, induce the phosphorylation of threonine 232 in c-Fos's activation domain, thereby potentiating its transactivation function. The invention relates to an isolated polypeptide characterized by having a molecular weight of 88 kD as determined by reducing SDS-PAGE, having threonine and serine kinase activity, and capable of phosphorylating the c-Fos activation domain.

The term "isolated" means any FRK polypeptide of the present invention, or any gene encoding a FRK polypeptide, which is essentially free of other poly-peptides or genes, respectively, or of other contaminants with which the FRK polypeptide or gene might normally be found in nature.

The invention includes a functional polypeptide, FRK, and functional fragments thereof. As used herein, the term "functional polypeptide" refers to a polypeptide which possesses a biological function or activity which is identified through a defined functional assay and which is associated with a particular biologic, morphologic, or phenotypic alteration in the cell. The biological function, for example, can vary from a polypeptide fragment as small as an epitope to which an antibody molecule can bind to a large polypeptide which is capable of participating in the characteristic induction or programming of phenotypic changes within a cell. An enzymatically functional polypeptide or fragment of FRK possesses c-Fos activation domain kinase activity, therefore, an in-gel kinase assay, for example, can be performed to identify a functional polypeptide. A "functional polynucleotide" denotes a polynucleotide which encodes a functional polypeptide as described herein.

Minor modifications of the FRK primary amino acid sequence may result in proteins which have substantially equivalent activity as compared to the FRK polypeptide described herein. Such modifications may be deliberate, as by site-directed mutagenesis, or may be spontaneous. All of the polypeptides produced by these modifications are included herein as long as the kinase activity of FRK is present. Further, deletion of one or more amino acids can also result in a modification of the structure of the resultant molecule without significantly altering its kinase activity. This can lead to the development of a smaller active molecule which would have broader utility. For example, it is possible to remove amino or carboxy terminal amino acids which may not be required for FRK kinase activity.

The FRK polypeptide of the invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides a synthetic peptide which binds to the c-Fos kinase, FRK. The amino acid sequence of SEQ ID NO:1, and conservative variations, comprises the synthetic peptide of the invention. This sequence represents amino acids of 226–236 of c-Fos polypeptide (FIG. 1; Sutherland, J. A., et al, *Genes & Dev.,* 6:1810, 1992) and includes Thr232 which is phosphorylated by FRK. As used herein, the term "synthetic peptide" denotes a peptide which does not comprise an entire naturally occurring protein molecule. The peptide is "synthetic" in that it may be produced by human intervention using such techniques as chemical synthesis, recombinant genetic techniques, or fragmentation of whole antigen or the like.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by the well known solid phase peptide synthesis methods described Merrifield, *J. Am. Chem. Soc.,* 85:2149, 1962), and Stewart and Young, *Solid Phase Peptides Synthesis*, (Freeman, San Francisco, 1969, pp. 27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The invention also provides polynucleotides which encode the FRK polypeptide of the invention and the synthetic peptide of SEQ ID NO:1. As used herein, "polynucleotide" refers to a polymer of deoxyribonucleotides or ribonucleotides, in the form of a separate fragment or as a component of a larger construct. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences.

DNA sequences of the invention can be obtained by several methods. For example, the DNA can be isolated using hybridization procedures which are well known in the art. These include, but are not limited to 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research,* 9:879, 1981).

The development of specific DNA sequences encoding FRK can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasimd- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., *Nucl. Acid Res.,* 11:2325, 1983).

A cDNA expression library, such as lambda gt11, can be screened indirectly for FRK polypeptide having at least one epitope, using antibodies specific for FRK. Such antibodies can be either polyclonally or monoclonally derived and used to detect expression product indicative of the presence of FRK cDNA. Polynucleotide sequences encoding a polypeptide having an amino acid sequence possessing at least one epitope to which an antibody to FRK binds, are included in the invention.

A polynucleotide sequence can be deduced from the genetic code, however, the degeneracy of the code must be taken into account. Polynucleotides of the invention include sequences which are degenerate as a result of the genetic code. The polynucleotides of the invention include sequences that are degenerate as a result of the genetic code. There are 20 natural amino acids, most of which are specified by more than one codon. Therefore, as long as the amino acid sequence of FRK results in a functional (e.g., retains kinase activity) polypeptide (at least, in the case of the sense polynucleotide strand), all degenerate nucleotide sequences are included in the invention.

The polynucleotide encoding FRK includes the full-length nucleotide sequence, as well as nucleic acid sequences complementary to that sequence. A complementary sequence may include an antisense nucleotide. When the sequence is RNA, the deoxynucleotides A, G, C, and T are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein under physiological conditions.

Since a polynucleotide sequence of the invention encodes essentially the entire FRK molecule it is now a matter of routine to prepare, subclone, and express smaller polypeptide fragments of polynucleotide from this or a corresponding polynucleotide sequence which would encode as few as one epitope for antibodies to FRK. The presence of such an epitope on a cloned polypeptide can then be confirmed using, for example, an antibody which binds to FRK.

The polynucleotide sequence for FRK also includes sequences complementary to the polynucleotide encoding FRK (antisense sequences). Antisense nucleic acids are DNA or RNA molecules that are complementary to at least a portion of a specific mRNA molecule (Weintraub, *Scientific American,* 262:40, 1990). The invention embraces all antisense polynucleotides capable of inhibiting production of FRK polypeptide. In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target FRK-producing cell. The use of antisense methods to inhibit the translation of genes is well known in the art (Marcus-Sakura, *Anal.Biochem.,* 172:289, 1988).

In addition, ribozyme nucleotide sequences for FRK are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med.-Assn.,* 260:3030, 1988). A major advantage of this approach is that, because they are sequence-specific, only mRNAs with particular sequences are inactivated.

There are two basic types of ribozymes namely, tetrahymena-type (Hasselhoff, *Nature,* 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The FRK polypeptides of the invention can also be used to produce antibodies which are immunoreactive or bind to epitopes of the FRK polypeptides. Antibodies of the invention also include antibodies which bind to the synthetic peptide in SEQ ID NO:1. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al, *Nature,* 256:495, 1975; *Current Protocols in Molecular Biology*, Ausubel, et al, ed., 1989).

The term "monoclonal antibody" refers to a population of one species of antibody molecule of determined (known) antigen-specificty. A monoclonal antibody contains only one species of antibody combining site capable of immunoreacting with a particular antigen and thus typically displays a single binding affinity for that antigen. A monoclonal antibody may therefore contain a bispecific antibody molecule having two antibody combining sites, each immunospecific for a different antigen.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction, $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: *A Laboratory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the FRK polypeptide of the invention can be prepared using an intact polypeptide or fragments containing small peptides of interest as the immunizing antigen. The polypeptide or a peptide such as SEQ ID NO:1 used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, in the present invention, an anti-idiotype antibody produced from an antibody which binds to the synthetic peptide of the invention can bind to the site on FRK which binds to c-Fos, thereby preventing FRK from binding to and phosphorylating c-Fos.

Polynucleotide sequences encoding the polypeptide or synthetic peptide (SEQ ID NO:1) of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

DNA sequences encoding the polypeptides can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the FRK polynucleotide sequences may be inserted into a recombinant expression vector. The term "recombinant expression vector" refers to a plasmid, virus or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyl-transferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XGPRT, gpt).

Transformation of a host cell with recombinant DNA may be carried out by conventional techniques which are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Examples of mammalian host cells include COS, BHK, 293, and CHO cells.

Isolation and purification of host cell expressed polypeptide, or fragments thereof, provided by the invention, may be carried out by conventional means including preparative chromatography and immunological separations involving monoclonal or polyclonal antibodies.

The FRK protein kinase of the invention is useful in a screening method for identifying compounds or compositions which affect the activity of the kinase. Thus, in another embodiment, the invention provides a method for identifying a composition which affects a c-Fos kinase comprising incubating the components, which include the composition to be tested and the kinase or a polynucleotide encoding the kinase, under conditions sufficient to allow the components to interact, then subsequently measuring the effect the composition has on kinase activity or on the polynucleotide encoding the kinase. The observed effect on the kinase may be either inhibitory or stimulatory. For example, the increase or decrease of kinase activity can be measured by adding a radioactive compound to the mixture of components, such as $^{32}$P-ATP, and observing radioactive incorporation into c-Fos or other suitable substrate for FRK, such as a peptide comprising SEQ ID NO:1, to determine whether the compound inhibits or stimulates protein kinase activity. A polynucleotide encoding the kinase may be inserted into an expression vector and the effect of a composition on transcription of the kinase can be measured, for example, by Northern blot analysis.

In another embodiment, the invention provides a method of treating a cell. proliferative disorder associated with FRK comprising administering to a subject with the disorder a therapeutically effective amount of reagent which modulates kinase activity. The term "therapeutically effective" means that the amount of peptide, monoclonal antibody or antisense nucleotide, for example, which is used, is of sufficient quantity to ameliorate the FRK associated disorder. The term "cell-proliferative disorder" denotes malignant as well as non-malignant cell populations which morphologically often appear to differ from the surrounding tissue. For example, the method may be useful in treating malignancies of the various organ systems, such as lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine and cancer of the esophagus.

The method is also useful in treating non-malignant or immunological-related cell-proliferative diseases such as psoriasis, pemphigus vulgaris, Behcet's syndrome, acute respiratory distress syndrome (ARDS), ischemic heart disease, post-dialysis syndrome, leukemia, rheumatoid arthritis, acquired immune deficiency syndrome, vasculitis, septic shock and other types of acute inflammation, and lipid histiocytosis. Essentially, any disorder which is etiologically linked to FRK kinase activity would be considered susceptible to treatment.

Treatment includes administration of a reagent which modulates FRK kinase activity. The term "modulate" envisions the suppression of expression of FRK when it is over-expressed, or augmentation of FRK expression when it is underexpressed. It also envisions suppression of phosphorylation of c-Fos, for example, by using the peptide of SEQ ID NO:1 as a competitive inhibitor of the natural c-Fos binding site in a cell. When a cell proliferative disorder is associated with FRK overexpression, such suppressive reagents as antisense FRK polynucleotide sequence or FRK binding antibody can be introduced to a cell. In addition, an anti-idiotype antibody which binds to a monoclonal antibody which binds a peptide of the invention may also be used in the therapeutic method of the invention. Alternatively, when a cell proliferative disorder is associated with underexpression or expression of a mutant FRK polypeptide, a sense polynucleotide sequence (the DNA coding strand) or FRK polypeptide can be introduced into the cell.

The antibodies of the invention can be administered parenterally by injection or by gradual infusion over time. The monoclonal antibodies of the invention can be administered intravenously, intraperitoneally, intramuscularly, subcutaneously, intracavity, or transdermally.

Preparations for parenteral administration of a peptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Polynucleotide sequences, including antisense sequences, can be therapeutically administered by various techniques known to those of skill in the art. Such therapy would achieve its therapeutic effect by introduction of the FRK polynucleotide, into cells of animals having the proliferative disorder. Delivery of FRK polynucleotide can be achieved using free polynucleotide or a recombinant expression vector such as a chimeric virus or a colloidal dispersion system. Especially preferred for therapeutic delivery of nucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a FRK sequence into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the FRK polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsitation. Helper cell lines which have deletions of the packaging signal include but are not limited to ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Another targeted delivery system for FRK polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The invention also provides a method for detecting a cell with FRK kinase activity a cell proliferative disorder associated with FRK comprising contacting a cell component with c-Fos kinase activity with a reagent which binds to the component and measuring the interaction of the reagent with the component. Such reagents can be used to measure relative levels of FRK expression compared to normal tissue. The cell component can be nucleic acid, such as DNA or RNA, or protein. When the component is nucleic acid, the reagent is a nucleic acid probe or PCR primer. The interaction of a nucleic acid reagent with a nucleic acid encoding a polypeptide with c-Fos kinase activity is typically measured using radioactive labels, however, other types of labels will be known to those of skill in the art. When the cell component is protein, the reagent is typically an antibody probe. The probes are directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

Preferably the probe for identification of a cell with FRK kinase activity is a c-Fos protein. FRK activity within a cell is measured by the amount of phosphorylation of the c-Fos protein probe. For example, the amount of FRK activity in a cell extract can be measured by mixing the extract with c-Fos protein or a peptide comprising SEQ ID NO:1, and adding a radioactive compound such as $^{32}$P-ATP to the mixture of components. The amount of radioactivity that is incorporated into the c-Fos reporter probe is determined, for example by SDS-PAGE, and compared to a cell control containing c-Fos and a normal level of FRK kinase activity.

The Fos protein used in the method of detection of the FRK kinase described above may exist as a single protein unit or a fusion protein. The fusion protein preferably consists of c-Fos and glutathione-S-transferase (GST) as a carrier protein. The c-fos nucleotide sequence is cloned 3' to the carrier protein in an expression vector, such as pGEX or such derivatives as pGEX2T or pGEX3X, the gene is expressed, the cells are lysed, and the extract is poured over a column containing a resin or mixed directly with a resin to which the carrier protein binds. When GST is the carrier, a glutathione (GSH) resin is used. When maltose-binding protein (MBP) is the carrier, an amylose resin is used. Other carrier proteins and the appropriate binding resin will be known to those of skill in the art.

The materials of the invention are ideally suited for the preparation of a kit. The kit is useful for the detection of the level of a c-Fos kinase comprising an antibody which binds a c-Fos kinase or a nucleic acid probe which hybridizes to FRK nucleotide, the kit comprising a carrier means being compartmentalized to receive in close confinement therein one or more containers such as vials, tubes, and the like, each of the container means comprising one of the separate elements to be used in the assay. For example, one of the container means may comprise a monoclonal antibody of the invention which is, or can be, detectably labelled. The kit may also have containers containing buffer(s) and/or a container comprising a reporter-means (for example, a biotin-binding protein, such as avidin or streptavidin) bound to a reporter molecule (for example, an enzymatic or fluorescent label).

The following examples are intended to illustrate but not limit the invention. While they are typical of those that might be used, other procedures known to those skilled in the art may alternatively be used.

EXAMPLES

Ras proteins exert their mitogenic and oncogenic effects through activation of downstream protein kinases (Egan, et al., *Nature,* 365:781–783, 1993). A major question is how Ras-generated signals reach the nucleus to activate downstream target genes. AP-1, a heterodimeric complex of Jun and Fos proteins, which activates mitogen-inducible genes (Angel, et al., *Biochem. Biophys. Acta.,* 1072:129–157, 1991), is a major nuclear target of Ras (Herrlich, et al., *Trends Genet,* 5:112–116, 1989). Recently, Ras- and UV-responsive protein kinases that phosphorylate c-Jun on serines (Ser) 63 and 73 and stimulate its transcriptional activity were identified (Hibi, et al., *Genes & Dev.,* 7:2135–2148, 1993). These proline-directed kinases, termed JNK, are novel MAP kinases (Derijard, et al, *Cell,* 75:1025–1037, 1994). A short sequence surrounding the major JNK phosphorylation site of c-Jun (Ser73) is conserved in c-Fos and is part of its activation domain (Sutherland, et al., *Genes & Dev.,* 6:1810–1819, 1992). The following Examples demonstrate that Ras does indeed augment c-Fos transcriptional activity through phosphorylation at Thr232, the homolog of Ser73 of c-Jun. However, this is mediated by a novel Ras- and mitogen-responsive proline-directed protein kinase that is different from JNKs and ERKs. Therefore, at least three types of proline-directed kinases (Thomas, Cell, 68:3, 1992) transmit Ras and mitogen generated signals to the transcriptional machinery.

EXAMPLE 1

Regulation of c-Fos Transcriptional Activity

Figure 1B:
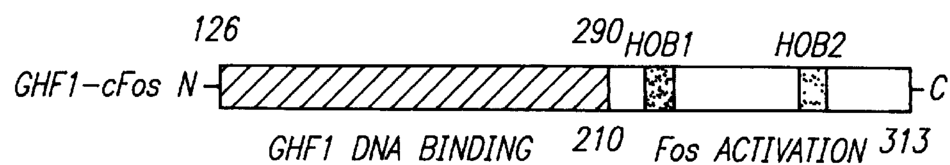
FIG. 1C shows Ras-, UV-, or TPA- induced activity of c-Fos.

The sequence surrounding the major JNK phosphorylation site in c-Jun is conserved in c-Fos (Sutherland, et al, supra), such that Thr232 is homologous to Ser73 in c-Jun (FIG. 1A). Both sequences correspond to the HOB1 regions of the Jun and Fos activation domains. To test whether the c-Fos activation domain is Ras-responsive, a fusion was generated between amino acids (AA) 210–313 of c-Fos (containing HOB1 and HOB2) and the DNA binding domain of GHF-1, a pituitary specific activator (Bodner, et al., *Cell,* 55:505–518, 1988). FIGS. 1A and B show diagrams illustrating the salient features of c-Fos and the GHF1-cFos (210–313) chimera, including the position of the HOB1 and HOB2 regions and a sequence alignment of the HOB1 regions of c-Jun and c-Fos.

F9 cells were transfected with 0.85 μg of a −237 rGH-LUC reporter, 0.35 μg of pSG-GHF1-cFos(210–313) or pSG-GHF1-cFos(210–313;S232A), and 0.75 μg pSG-Ha-Ras(Leu61) expression vectors per 35 mm well. To construct GHF1-cFos(210–313), a 1.4 kb HindIII-HpaI fragment from cJ/GHF-1 (Binetruy, et al., *Nature,* 351:122–127, 1991) was cloned into pSG6 between the HindIII and SmaI sites. pSG6 is derived from pSG5 (Green, et al, *Nucleic Acids Res.* 16:369, 1988) and contains a sequence from the HincII to the BamHI site of pBluescript cloned between the EcoRI and BamHI sites of pSG5. The c-Jun coding region was replaced by the Flag epitope (Ellis, et al., *Cell,* 45:721–732, 1986). The last two codons and the stop codon of GHF-1 were modified by site-directed mutagenesis to create an NcoI site. The codons encoding AA209/210 and 313/314 of mouse c-Fos were modified by site-directed mutagenesis to generate NcoI and BamHI sites, respectively. The resultant 312 bp NcoI-BamHI fragment containing AA210–313 of mouse c-Fos was inserted between NcoI site created at the end of the GHF-1 coding region and a downstream BamHI site to generate GHF1-cFos(210–313). GHF1-cFos (210–313;T232A) is identical to GHF1-cFos(210–313) except that it contains a threonine (Thr) to alanine (Ala) substitution at position 232 introduced by site-directed mutagenesis. The -237 rGH-LUC reporter was made by inserting a 255 bp HindIII-BstYI fragment of rat GH-CAT (West, et al., *Mol. Cell. Biol.,* 7:1193–1197, 1987) between the HindIII and BamHI sites in the polylinker region of p20LUC (Feigner, et al., *Proc. Natl. Acad. Sci. USA,* 84:7413–7418, 1987).

A portion of the cells were treated with TPA (100 ng/ml) or UV (80J/m$^2$), as indicated. The treated cells were harvested 8 hours later and assayed for LUC activity. One unit of relative activity is equivalent to five-fold activation by GHF1-cFos(210–313) over the basal level of reporter activity in the presence of "empty" expression vector. The averages of four different experiments were determined.

Figure 1C:
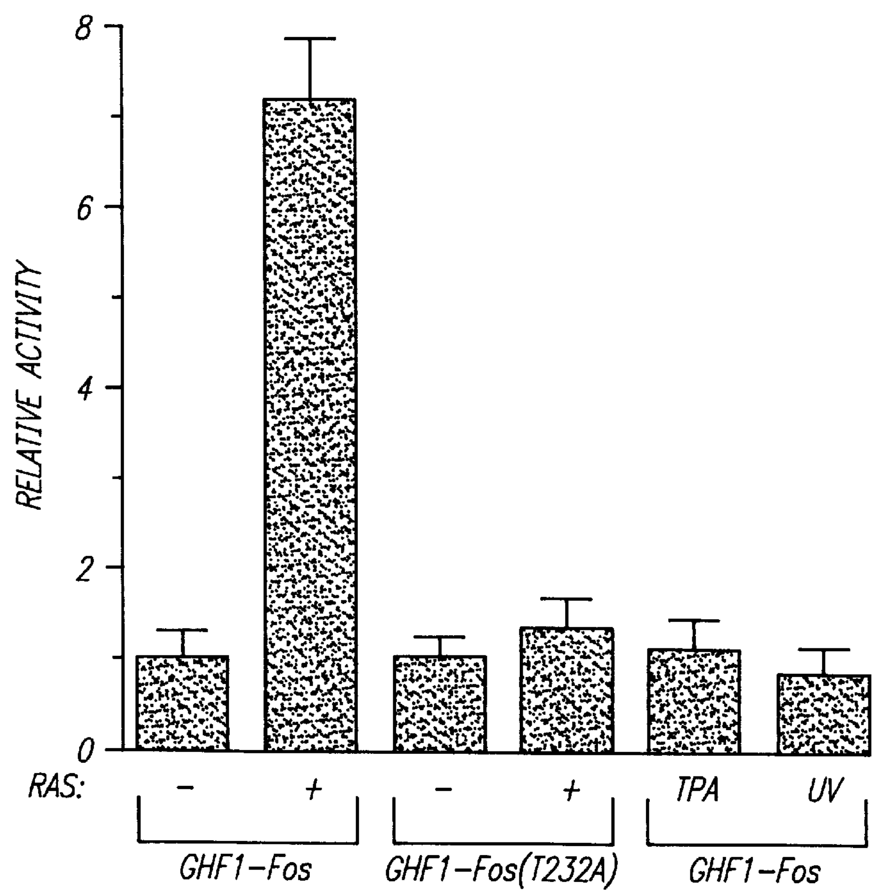

Cotransfection experiments indicated that GHF1-cFos (210–313) activated the rGH-LUC reporter and its activity was stimulated 7-fold by oncogenic Ha-Ras (FIG. 1C). Both the basal and the Ras-induced activities of GHF1-cFos (210–313) are similar to those of a cJun-GHF1 chimera (Binetruy, et al., supra). Substitution of Thr232 by an Ala residue had no effect on the basal activity of GHF1-cFos (210–313;T232A) but abolished its response to Ha-Ras. Since Ha-Ras does not affect GHF-1 DNA binding activity (Smeal, et al., *Mol. Cell. Bio.,* 12:3507–3513, 1992), the enhancement of GHF1-cFos(210–313) activity is due to potentiation of the c-Fos activation function.

In addition to Ha-Ras, the transcriptional activity of c-Jun is stimulated by UV irradiation (Devary, et al., *Cell,* 71:1081–1091, 1992), which results in strong activation of JNK (Hibi, et al, supra; Derijard, et al., supra). However, activation by GHF1-cFos(210–313) was not potentiated by UV irradiation, or 12–0-tetradecanoyl phorbol 13-acetate (TPA, FIG. 1C). These results suggested that, despite the similarity between the HOB1 regions of c-Jun and c-Fos, the kinase that phosphorylates Thr232 was different from the JNKs, whose activity is stimulated more efficiently by UV irradiation than by Ha-Ras expression. Since TPA is an efficient activator of ERK1 and 2 (Thomas, et al., *Cell,* 68:1031–1040, 1992), these kinases are also unlikely to be responsible for Thr232 phosphorylation.

EXAMPLE 2 c-Fos Phosphorylation Contributes to AP-1 Activation

Ha-Ras potentiates activation by c-Jun homodimers (Binetruy, et al., supra; Smeal, et al., supra) and increases endogenous AP-1 activity (Herrlich, et al., supra; Wasylyk, et al., *EMBO J.,* 7:2475–2483, 1988; Schonthal, et al., *Cell,* 54:325–334, 1988). By dimerizing with c-Jun, c-Fos is an important contributor toAP-1 activity (Chiu, et al., *Cell,* 54:541–552, 1988; Sassone-Corsi, et al., *Cell,* 54:553–560, 1988; Kouzarides, et al., *Nature,* 336:646–656, 1988; Smeal, et al., *Genes & Dev.,* 3:2091–2100,1989). Therefore, a c-Jun:c-Fos heterodimer was examined to determine whether it also responds to Ha-Ras.

Figure 2:
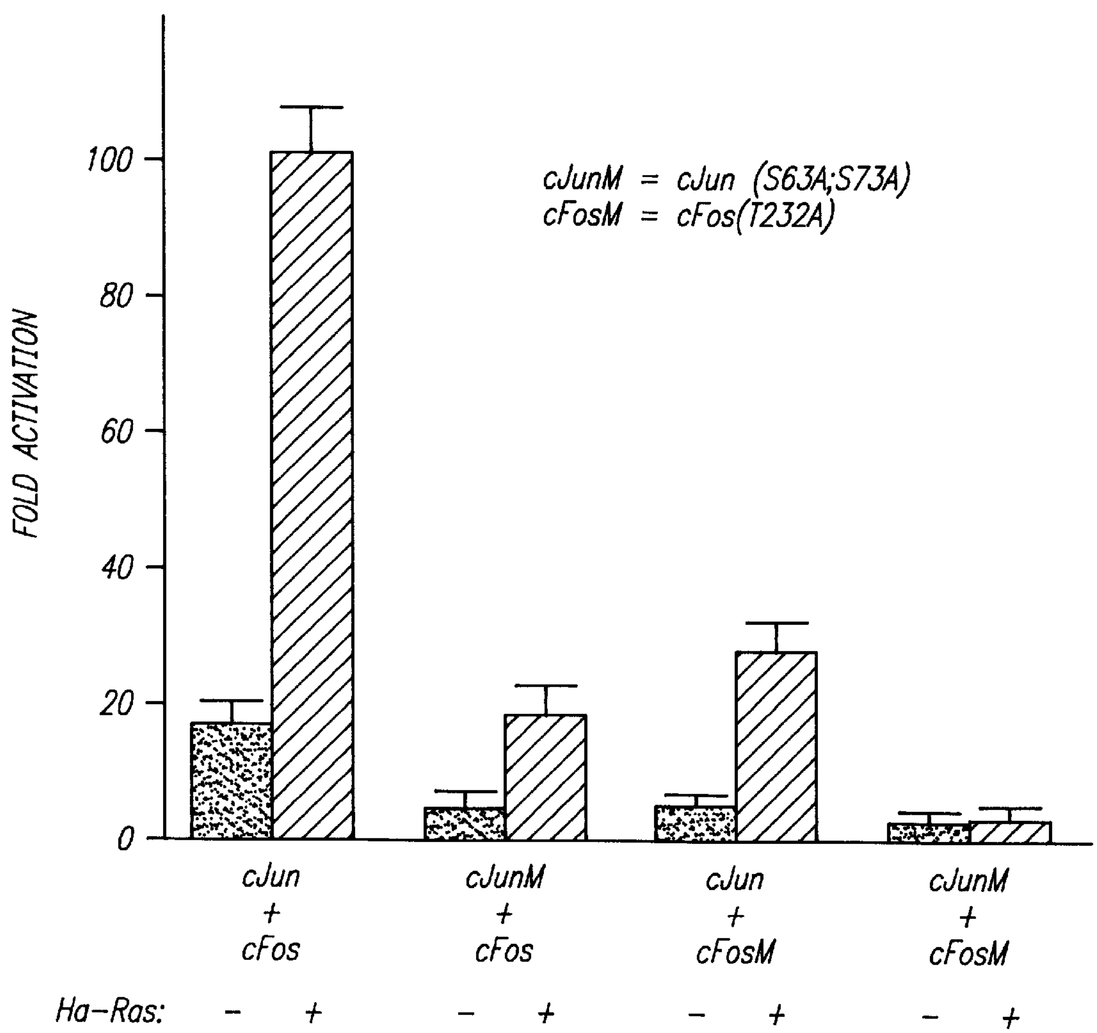
FIG. 2 shows transactivation of c-Fos constructs in the presence or absence of Ha-Ras.

F9 cells were transfected with 0.3 μg of –73 Col-LUC (Deng, et al., *Genes & Dev.,* 7:479, 1993) and 0.15 μg of either RSV-cJun, RSV-cJun(S63A;S73A), pSV40-cFos (mouse) or pSV40-cFos(T232A) with or without 0.3 μg of pSG-Ha-Ras(Leu61) per 35 mm well, as indicated. The averages of two experiments (each in duplicate) are shown in FIG. 2. Fold activation was determined by dividing the actual luciferase activity obtained in the presence of the Jun and Fos expression vectors to the activity obtained when the reporter was contransfected with an "empty" expression vector (pRSV-O).

Transactivation of the AP-1 responsive –73Col-LUC reporter by c-Fos plus c-Jun was, indeed, stimulated by Ha-Ras (FIG. 2). Transactivation by wild type (wt) c-Fos in combination with c-Jun lacking the JNK phosphorylation sites, c-Jun(S63A;S73A), and by c-Fos(T232A) plus wt c-Jun was also stimulated by Ha-Ras. However, transactivation of –73Col-LUC by c-Fos(T232A) plus c-Jun (S63A;S73A) was no longer Ha-Ras responsive. This result suggests that phosphorylation at Thr232 is required for Ha-Ras responsiveness when c-Fos is complexed with its physiological partner, c-Jun. Substitution of Thr232 by Ala and/or Ha-Ras expression had no effect on accumulation of c-Fos or its interaction with c-Jun.

EXAMPLE 3

Phosphorylation of Thr232 is Ras-Responsive in vivo

Transient coexpression of oncogenic Ha-Ras with c-Fos resulted in increased phosphorylation of wt c-Fos but not of c-Fos(T232A). Two-dimensional mapping (Boyle, et al., *Meth. Enzym.,* 201:110–149, 1991) of tryptic peptides derived from wt c-Fos and c-Fos(T232A) confirmed these observations and indicated that Thr232 is the major Ha-Ras responsive phosphoacceptor of c-Fos.

F9 cells were transfected with 10 μg of expression vectors encoding wt c-Fos or c-Fos(T232A) in the absence or presence of 10 μg of pSG-Ha-Ras(Leu61), as indicated. Equal numbers of cells were labelled 12 hours after transfection for 4 hours with $^{32}$-P orthophosphate (0.5 mCi/ml). c-Fos proteins were purified by immunoprecipitation using a monoclonal antibody (de Togni, et al., *Mol. Cell. Biol.,* 8:2251–2256, 1988) and subjected to two-dimensional phosphopeptide analysis, as described (Boyle, et al., supra). Maps were exposed to preflashed x-ray films for three days. 1, 2, 3 and 4 refer to major phosphopeptides that migrate similarly to phosphopeptides previously shown to be derived from the C-terminal region of c-Fos (Tratner, et al., *Mol. Cell. Biol,* 12:998–1006, 1991). R is the phosphopeptide which is most dramatically stimulated by Ha-Ras (FIG. 3A).

Most of the Ha-Ras mediated increase in c-Fos phosphorylation was localized to tryptic peptide R. Phosphopeptide R was missing in c-Fos(T232A), indicating that it arises from phosphorylation of Thr232. Furthermore, the migration position of this peptide is entirely consistent with its predicted amino acid composition (Boyle, et al., supra). The predicted R phosphopeptide is 41 AA long because of cleavage between Asp246 and Pro247 by performic acid (Landon, *Meth. Enzym.,* 47:145–149, 1977). This peptide is neutral in the pH1.9 electrophoresis buffer and has a high $R_f$ value (0.46) in the chromatography system used (Boyle, et al., supra). Furthermore, phosphoaminoacid analysis revealed the presence of phosphothreonine in the R peptide of wt c-Fos.

To confirm this assignment, the response of a c-Fos (T232S) mutant to Ha-Ras was examined. F9 cells were transfected with 10 μg of expression vectors encoding wt c-Fos or c-Fos(T232S) in the absence or presence of 10 μg of pSG-Ha-Ras(Leu61), as indicated. The cells were labeled and processed as described above. R and R' refer to the phosphopeptides which are most dramatically elevated in Ha-Ras expressing cells and are derived from wt c-Fos and c-Fos(T232S), respectively. Coexpression of Ha-Ras stimulated the phosphorylation of c-Fos(T232S) resulting in appearance of phosphopeptide R' (FIG. 3B).

Figure 3A:
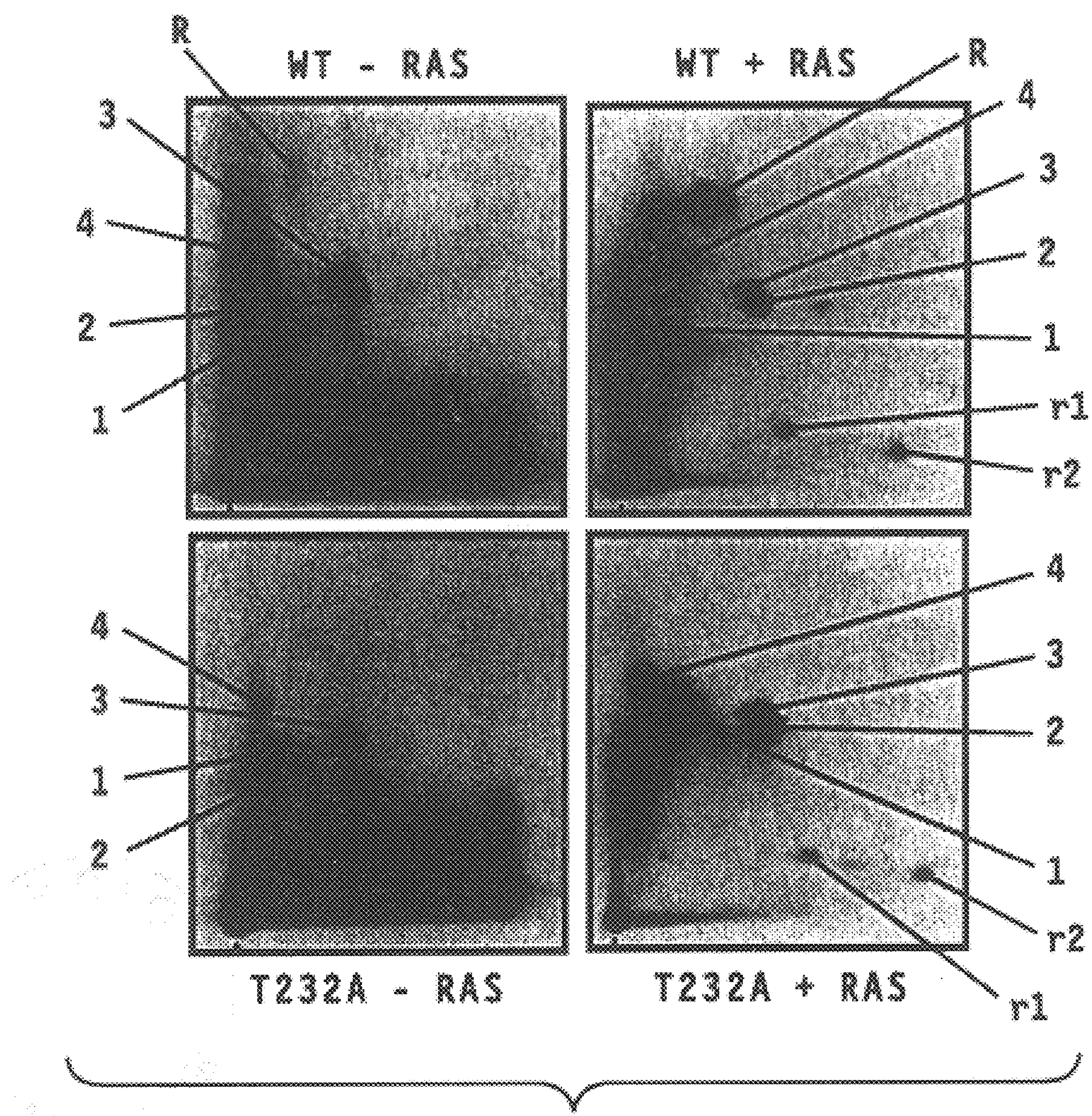
FIGS. 3A–C show 2-D phosphopeptide analysis after stimulation of c-Fos phosphorylation on Thr232 by co-expression of activated Ha-Ras.
Figure 3B:
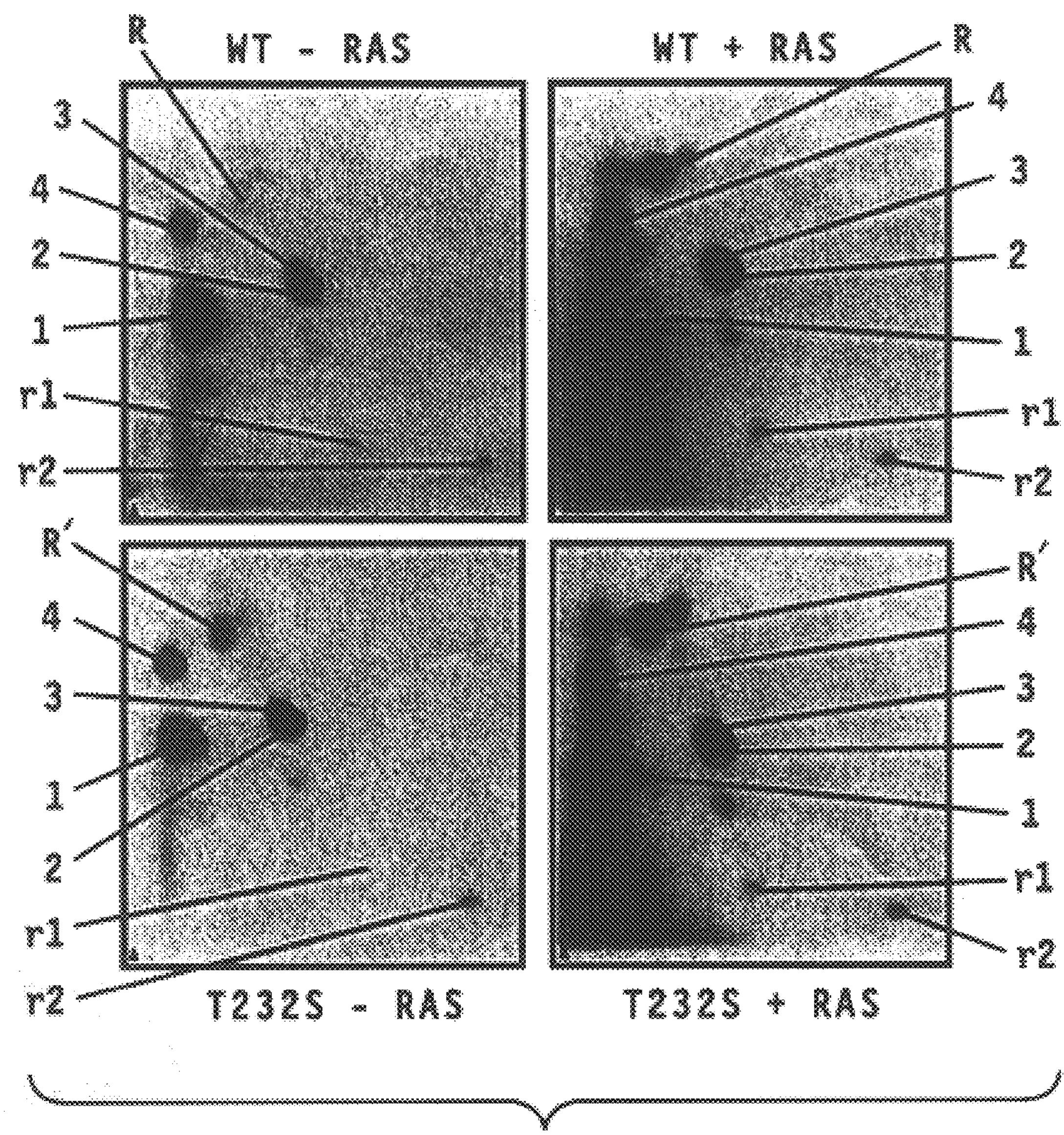
Figure 3C:
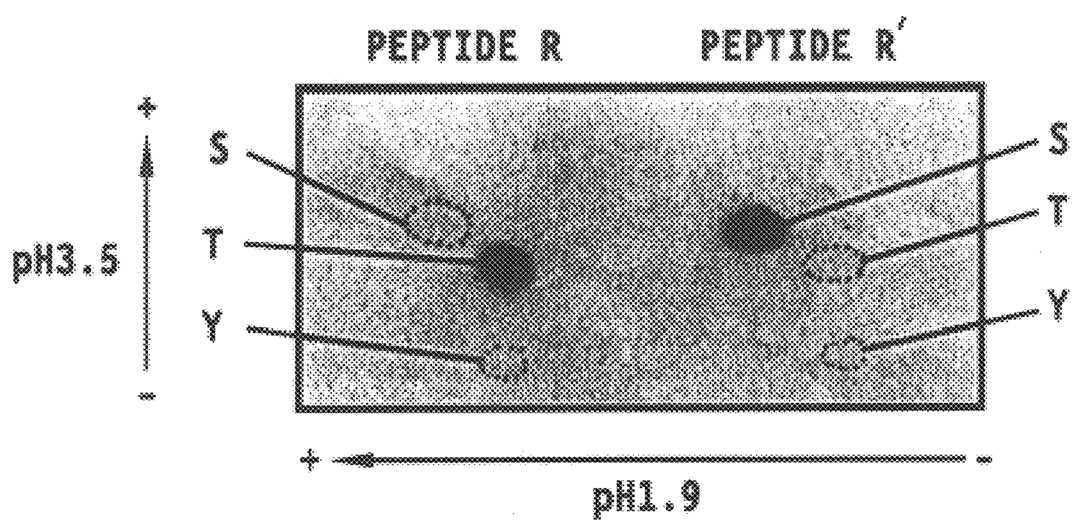

The R and R' phosphopeptides from the chromatograms shown in FIGS. 3A and 3B were extracted from the plates and subjected to partial acid hydrolysis and analyzed by two-dimensional high-voltage electrophoresis as described (Boyle, et al., supra). The directions of the electrophoretic separation are indicated (FIG. 3C). $^{32}$P-labeled phosphoaminoacids were detected by exposure to preflashed x-ray film, using an intensifying screen for 8 days at −80° C. Nonradioactive phosphoaminoacid standards were detected by ninhydrin staining (FIG. 3C). Phosphoaminoacid analysis indicated that whereas phosphopeptide R contained phosphothreonine, phosphopeptide R' contained phosphoserine (FIG. 3C). Ha-Ras expression also led to a slight and variable increase in phosphopeptides r1 and r2, derived from wt c-Fos, and decreased the level of others (FIGS. 3A and 3B). These changes were also observed with c-Fos(T232A). Phosphoaminoacid analysis revealed the presence of phosphoserine in both r1 and r2.

EXAMPLE 4 c-Fos is Phosphorylated by a Novel Ras and Mitogen Activated Kinase

Agents that activate either JNK or ERK½, other than Ha-Ras, do not stimulate GHF1-cFos activity as shown in FIG. 1C. To further investigate this point, the effect of UV and TPA on c-Fos phosphorylation was examined. Human c-Jun was prepared as described (Deng, et al., supra) and mouse c-Fos (both wt and mutant) was prepared using the same expression system. Both proteins were purified to near homogeneity. The recombinant c-Jun and c-Fos proteins were incubated at 30° C. for 30 minutes with the relevant kinases in kinase buffer (20 mM Hepes pH 7.6, 10 mM $MgCl_2$, 20 mM β-glycerophosphate, 20 mM p-nitrophenylphosphate, 0.1 mM $NaVO_4$, 2 mM DTT) containing 10 μM $\gamma^{32}$P-ATP in a 20 μl volume. The reactions were terminated by addition of 6.5 μl 4×SDS-PAGE sample buffer and boiling. Purified ERK½ is a mixture of both enzymes (a gift from Dr. M. Cobb). Polyclonal anti-JNK1 antiserum was prepared against recombinant JNK1 and was used to immunopurify activated JNK1 from UV-irradiated HeLa cells. Immunoprecipitations were performed as described (Derijard, et al., *Cell,* 75:1025–1037, 1994).

Figure 4A:
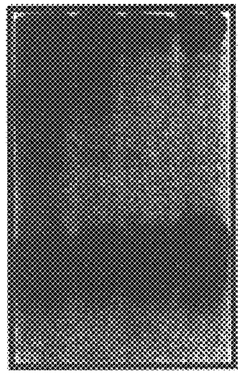
FIG. 4A shows SDS-PAGE of c-Fos immunoprecipitates after in vivo phosphorylation of c-Fos. (C=control; T=TPA (100 ng/ml); U=UV irradiation; R=cotransfection with pSG-Ha-Ras-Leu61).

FIG. 4A shows the analysis of in vivo phosphorylation of c-Fos. Wt c-Fos expression vector was transiently transfected into F9 cells that were treated as indicated. C:control; T:TPA (100 ng/ml) treatment for 15 minutes before harvest; U:UV irradiation (80 J/m$^2$), 30 minutes before harvest; R:cotransfection with pSG-Ha-Ras(Leu61) as described in EXAMPLE 3 (FIG. 3). Cells were labeled and processed as described in EXAMPLE 3 (FIG. 3). The c-Fos immunoprecipitates were separated by SDS-PAGE and autoradiographed.

By contrast to Ha-Ras, UV and TPA had a marginal effect on c-Fos phosphorylation (FIG. 4A). The small increase in total c-Fos phosphorylation after TPA or UV exposure was restricted to phosphopeptides 2 and 4, and no changes in phosphopeptide R were detected. TPA, however, activated ERK2, whereas UV irradiation activated JNK1. It is therefore unlikely that either the ERKs or the JNKs phosphorylate c-Fos at Thr232. This assertion is further supported by in vitro phosphorylation experiments.

Figure 4B:
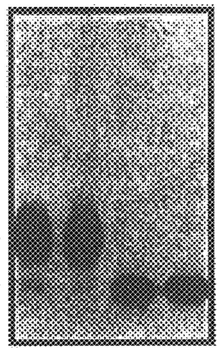
FIG. 4B shows SDS-PAGE of phosphorylation of c-Fos and c-Jun after treatment with JNK1 or ERK½. (W=wild-type c-Fos; M=c-fos (T232A)).

Recombinant c-Fos or c-Fos(T232A) (50 ng each) was mixed with recombinant c-Jun (40 ng) and incubated at 30° C. for 30 minutes with immunopurified JNK1 or purified ERK½ (a mixture of both enzymes) in kinase buffer containing γ-32-ATP. The reactions were terminated by addition of 6.5 μl 4×SDS-PAGE sample buffer and boiling. W:wt c-Fos, M:c-Fos(T232A). The phosphorylated proteins were separated by SDS-PAGE and visualized by autoradiography. The bands corresponding to c-Jun and c-Fos are indicated. Using c-Jun:c-Fos heterodimers as substrates, ERK½ (a mixture of both enzymes) phosphorylated wt c-Fos and c-Fos(T232A) with similar efficiencies (FIG. 4B).

Figure 4C:
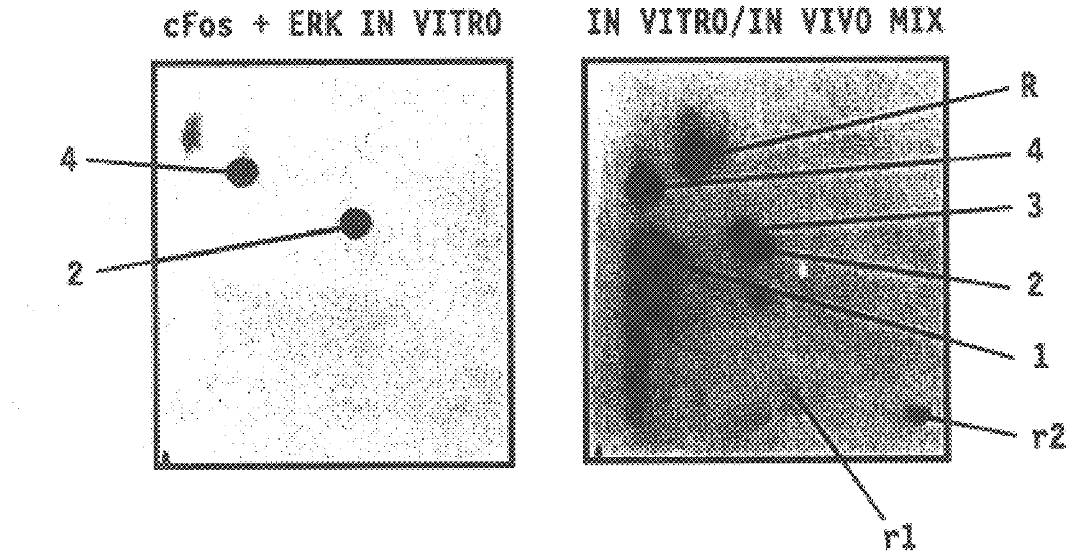
FIG. 4C shows a 2-D tryptic peptide map of wild-type c-Fos phosphorylated in vitro by ERK½ and 1:1 mixture between c-Fos phosphorylated in vitro by ERK½ and c-Fos labeled in vivo and isolated from Ha-Ras cotransfected cells.

Two-dimensional tryptic peptide maps of wt c-Fos phosphorylated in vitro by ERK½ as described above and a 1:1 mixture between c-Fos phosphorylated in vitro by ERK½ and c-Fos labeled in vivo and isolated from Ha-Ras cotransfected cells. As revealed by peptide mapping phosphorylation by ERK½ gave rise to phosphopeptides 2 and 4, which are also phosphorylated in vivo (FIG. 4C). The low level of c-Jun phosphorylation by ERK½ occurs at Ser243, as previously reported (Alvarez, et al., *J. Biol Chem.,* 266:15297, 1991). JNK1, on the other hand, phosphorylated c-Jun very efficiently but did not phosphorylate c-Fos.

EXAMPLE5

Regulation of c-Fos Transcriptional Activity by EGF

To identify the Ras-responsive protein kinase that phosphorylates Thr232 a cell line, A431, in which c-Ha-Ras is efficiently activated by epidermal growth factor (EGF) (Buday, et al., *Cell,* 73:611–620, 1993) was utilized. First it was determined whether c-Fos transcriptional activity was regulated by EGF.

Figure 5A:
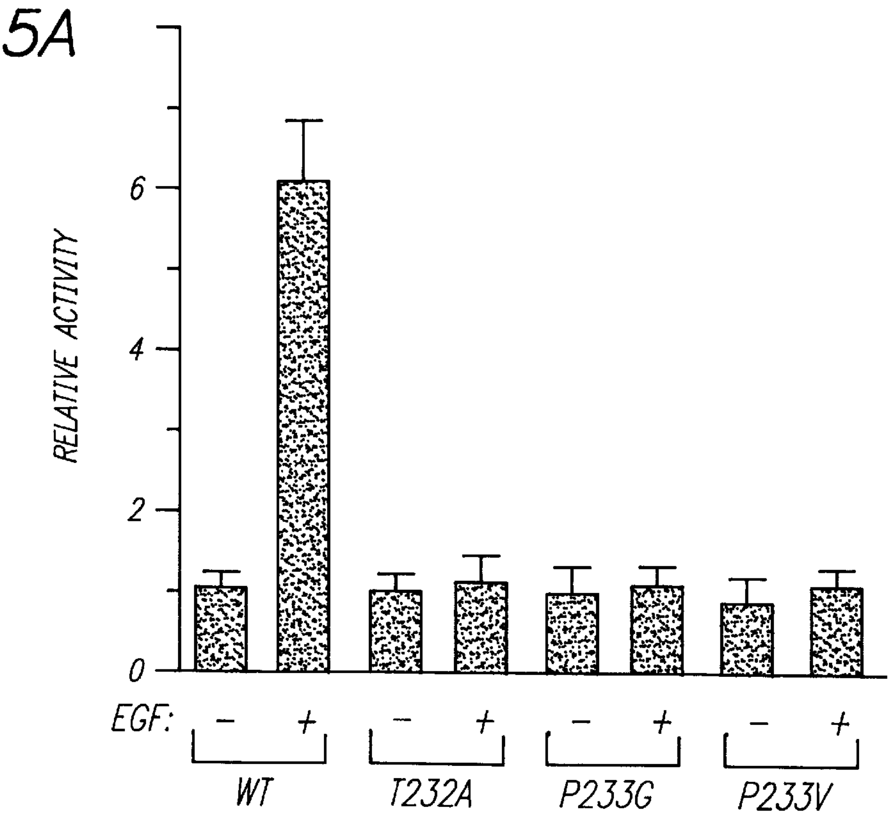
FIGS. 5A and 5B shows Luc reporter activity indicating c-Fos transcriptional activity after treatment with or without EGF.

A431 cells on 60 mm dishes were transfected with 1 μg of a −237 rGH-LUC reporter together with 1 μg of SRα expression vectors encoding: GHF1-cFos(210–313), GHF1-cFos(210–313; T232A), GHF1-cFos(210–313;P233G) or GHF1-cFos(210–313; P233V), using the lipofection procedure (Felgner, et al., supra). After 48 hours cells were either treated with EGF (100 ng/ml) or left untreated and harvested 8 hours later for determination of LUC activity. The averages of three different experiments are shown. Using the GHF1-cFos(210–313) construct, 6-fold stimulation by EGF was observed (FIG. 5A). This stimulation is likely to be dependent on phosphorylation at Thr232, as GHF1-cFos (210–313;T232A) was not responsive to EGF. Thr232 is followed by a Pro residue, suggesting it is recognized by a proline-directed kinase (Thomas, supra). Indeed, substitution of Pro233 by either a Gly or a Val residue abolished the responses to EGF (FIG. 5A) and Ha-Ras.

Figure 5B:
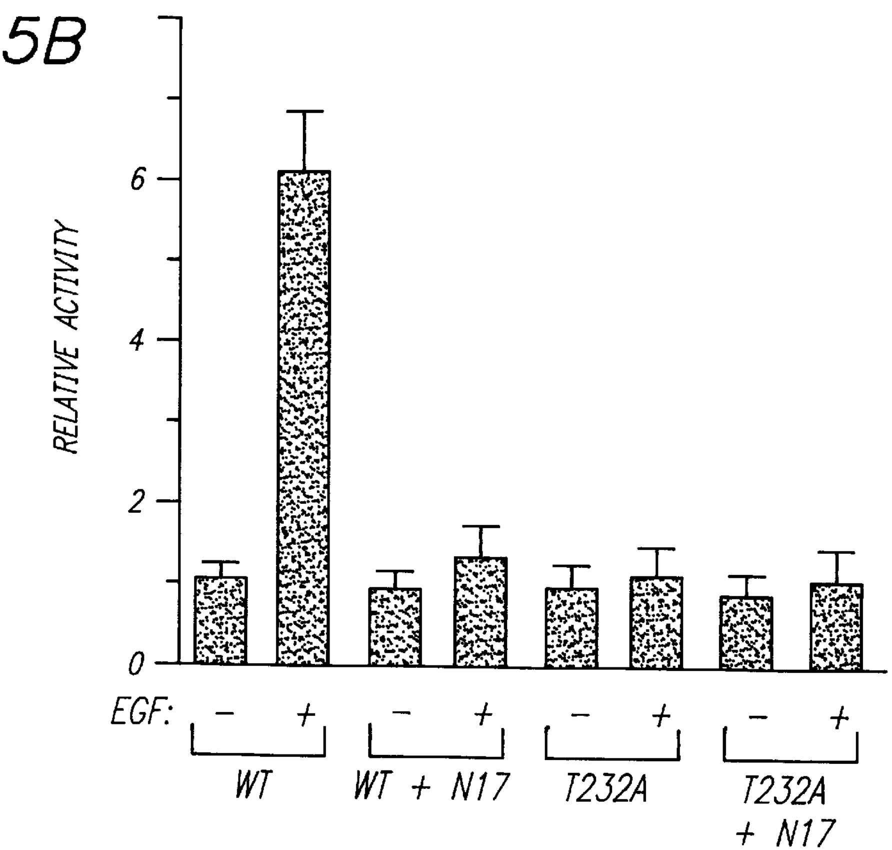

A431 cells on 60 mm dishes were transfected with 1 μg of a −237 rGH-LUC reporter together with 1 μg of SRα expression vectors encoding GHF1-cFos(210–313) or GHF1-cFos(210–313;T232A) in the absence or presence of 3 μg of SRa-Ras(Asn17), as described above. As suggested by its inhibition by coexpression of the dominant negative Ha-Ras (Asn17) mutant (Smeal, et al, *Mol. Cell. Biol.,* 12:3507–3513, 1992; Feig, et al, *Mol. Cell. Biol.,* 8:3235–3243, 1988), the stimulation of c-Fos transcriptional activity by EGF is Ras-dependent (FIG. 5B).

EXAMPLE 6

Indentification of the Mitogen-activated Kinase Phosphorylating c-Fos at Thr232

Extracts of EGF stimulated A431 cells were examined for the presence of a protein kinase activity specific for Thr232 using the in-gel kinase assay (Kameshita, et al., *Anal. Biochem.,* 183:139–143, 1989). Whole cell extracts (100 μg each) of A431 cells treated with EGF (E, 100 ng/ml for 15 minutes) or untreated (C) were separated on SDS-polyacrylamide gels containing immobilized c-Fos, GST-cFos(210–313), GST-cFos(210–313;T232A) or GST proteins. The gels were subjected to renaturation and in-situ phosphorylation as described (Hibi. et al, supra). The 88 kD band corresponding to FRK is indicated. Whole cell extracts of EGF-treated (E), EGF+dexamethasone (D +E) treated or untreated (C) PC12[Ha-Ras(Asn17)] cells (Szeberenyi, et al., *Mol Cell. Biol.,* 10:5324–5332, 1990) were analyzed by the in-gel kinase assay as described above with immobilized c-Fos as a substrate. These cells were either untreated or treated with dexamethasone ($10^{-6}$ M) for 3 hours, as indicated, and then exposed to EGF (100 nglml), as indicated, for 15 minutes prior to harvesting. The migration position of FRK is indicated.

Figure 6A:
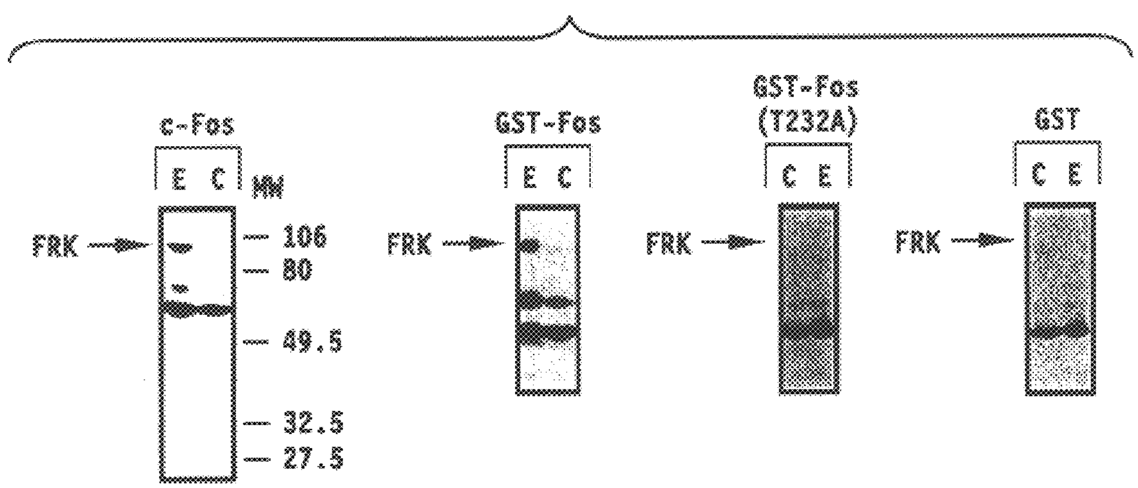
FIG. 6A shows an in-gel kinase assay identifying the mitogen-activated kinase phosphorylating c-Fos at Thr232. The 88 kD band corresponding to FRK is indicated.
Figure 6B:
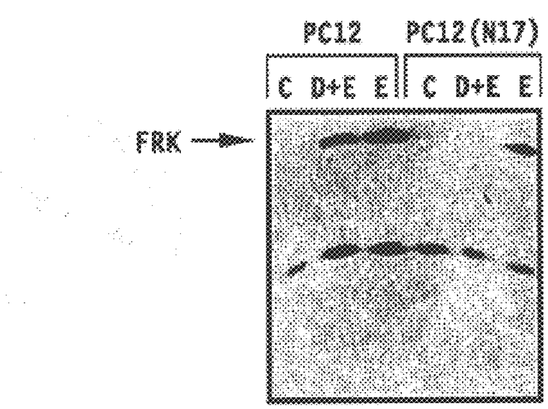
FIG. 6B shows whole cell extracts analyzed by an in-gel kinase assay after treatment of cells with EGF (E), EGF and dexamethasone (D and E) or untreated (C) PC12[Ha-Ras (Asn17)].

Incubation of A431 cells with EGF resulted in rapid activation of an 88 kD protein kinase activity, termed FRK (Fos Regulating Kinase), that phosphorylated c-Fos or GST-cFos substrates which were incorporated into the gel (FIG. 6A). The 88 kD FRK has also been detected in EGF-treated F9, COS, HeLa and PC12 cells (FIG. 6B). In a PC12 derivative containing an inducible Ha-ras(asnl7) allele, (Szeberenyi, et al., supra), activation of FRK by EGF was inhibited by induction of Ha-Ras(Asn17), further substantiating the conclusion it is a Ras-dependent kinase (FIG. 6B). FRK activity was not detected in the absence of c-Fos or when either c-Jun, GST or GST-cFos(T232A) were used as substrates (FIG. 6A).

Figure 6C:
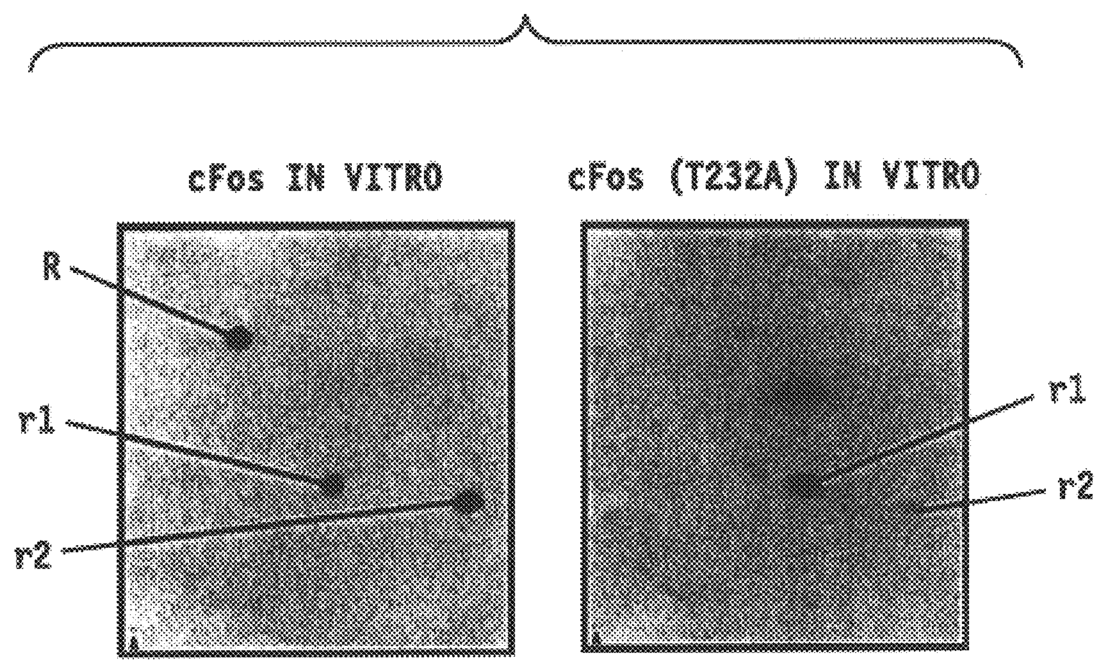
FIG. 6C shows phosphopeptide mapping of c-Fos and c-Fos (T232A) phosphorylated by FRK.

In-gel kinase assays using extracts of EGF-stimulated A431 cells and either wt c-Fos or c-Fos(T232A) substrates were performed as described above. The 88 kD bands corresponding to FRK-phosphorylated c-Fos proteins were excised and subjected to tryptic phosphopeptide mapping (Boyle, et al., supra Shown are the maps of wt c-Fos and c-Fos(T232A) phosphorylated by FRK. Phosphopeptide mapping indicated that phosphorylation by FRK occurred on peptides R, r1 and r2 (FIG. 6C), the same phosphopeptides detected after Ha-Ras coexpression (FIG. 3). Using full length c-Fos(T232A) as a substrate, the same kinase activity was detected but, as indicated by phosphopeptide mapping, phosphorylation occurred only on peptides r1 and r2 (FIG. 6C). Therefore, the EGF-activated 88 kD FRK is specific for Thr232 and the two secondary Ras-responsive phosphorylation sites. Since substitution of Pro233 by Gly prevented phosphorylation of Thr232, FRK is a proline-directed kinase.

These experiments demonstrate that activated Ha-Ras augments c-Fos transcriptional activity by stimulating its phosphorylation on Thr232. Unexpectedly, the protein kinase that phosphorylated c-Fos at Thr232 is neither JNK1 (46kD in size) nor JNK2 (55 kD in size), which phosphorylate c-Jun at the Ras-responsive sites, Ser63 and 73 (Hibi, et al., supra; Derijard, et al., supra). This conclusion is based on the inability of UV irradiation, a potent JNK activator (Hibi, et al., supra; Derijard, et al., supra), to induce c-Fos phosphorylation in vivo, and the failure of immunopurified JNK1 to phosphorylate c-Fos in vitro. In addition, TPA, a potent activator of ERK1 and 2 (Thomas, et al, supra), does not stimulate Thr232 phosphorylation in vivo and purified ERK½, although being efficient c-Fos kinases, do not phosphorylate it at Thr232. Therefore, while the mitogen-responsive kinase that phosphorylates c-Fos at Thr232 is proline-directed, like the JNKs and ERKs, it is a different enzyme.

Concurrently, the invention shows that EGF-stimulation results in rapid activation of an 88 kD protein kinase that phosphorylates c-Fos at Thr232. In addition to its EGF and Ras responsiveness, like the other MAP kinases, this protein kinase, termed FRK, is proline-directed kinase. Preliminary evidence suggests that the two secondary FRK phosphopeptides (r1, r2) contain Ser133 and are due to cleavage at Lys139 and Arg140, respectively. Ser133 is also followed by a Pro and is located within a sequence similar to that surrounding Thr232. Despite the size similarity to RSK (Blenis, *Cancer Cells,* 3:445–449, 1991), another mitogen-responsive kinase that phosphorylates c-Fos (Chen, et al., *Proc. Natl. Acad. Sci. USA,* 90:10952–10956, 1993), FRK is different enzyme. First, RSK is not proline-directed (Stokoe, et al, *Biochem. J.* 296:843–849, 1993; Kemp, et al., *Trend Biochem. Sci.* 15:312–316, 1990), while FRK is. In fact, Pro insertion at position P+1 inhibits phosphorylation by RSK (Stokoe, et al, supra). Second, the RSK consensus includes basic residues (Stokoe, et al., supra; Kemp, et al., supra), which are absent from the immediate surrounding of Thr232. Third, RSK phosphorylates c-Fos at Ser362 (Chen, et al., supra), which can be deleted without affecting phosphorylation by FRK.

The foregoing is meant to illustrate, but not to limit, the scope of the invention. Indeed, those of ordinary skill in the art can readily envision and produce further embodiments, based on the teachings herein, without undue experimentation.

We claim:

1. An antibody which binds to a polypeptide characterized by (a) having a molecular weight of 88 kD as determined by reducing SDS-PAGE;

(b) having threonine and serine kinase activity; and (c) phosphorylating the c-Fos activation domain.

2. The antibody of claim 1, wherein the antibody is polyclonal.

3. The antibody of claim 1, wherein the antibody is monoclonal.

4. An antibody which binds to the amino acid sequence of SEQ ID NO:1.

5. The antibody of claim 4, wherein the antibody is polyclonal.

6. The antibody of claim 5, wherein the antibody is monoclonal.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (ix) FEATURE:

-continued

```
        (A) NAME/KEY: Peptide
        (B) LOCATION: 1..11

    (xi) SEQUENCE DESCRIPTION: SEQ ID NO:1:

Gly Leu Pro Glu Ala Ser Thr Pro Glu Ser Glu
1               5                   10
```